United States Patent [19]

Hirsch et al.

[11] Patent Number: 4,507,875
[45] Date of Patent: Apr. 2, 1985

[54] APPARATUS FOR DETERMINING THE CONCENTRATION OF VAPORS IN A FLOWING GAS STREAM

[75] Inventors: Werner Hirsch, Celle; Uwe Ehling, Elmshorn, both of Fed. Rep. of Germany

[73] Assignee: B.A.T. Cigaretten-Fabriken GmbH, Hamburg, Fed. Rep. of Germany

[21] Appl. No.: 509,870

[22] Filed: Jun. 30, 1983

[30] Foreign Application Priority Data

Jul. 1, 1982 [DE] Fed. Rep. of Germany ....... 3224506

[51] Int. Cl.$^3$ ............................................. F26B 21/06
[52] U.S. Cl. .......................................... 34/44; 34/46; 34/48; 34/50; 34/54; 73/29; 236/44 R; 236/44 C
[58] Field of Search ..................... 34/44, 46, 50, 57 R, 34/48, 54; 73/29, 73, 76, 196; 131/303; 236/44 R, 44 A, 44 C

[56] References Cited

U.S. PATENT DOCUMENTS 2,695,514 11/1954 Brown ............................. 236/44 R
4,090,179 5/1978 Hirano ................................. 73/196
4,221,058 9/1980 Zagorzycki ............................ 34/50

FOREIGN PATENT DOCUMENTS 2846826 10/1980 Fed. Rep. of Germany .
3114712 2/1982 Fed. Rep. of Germany .

OTHER PUBLICATIONS

Mulsow, Robert, "Direkte Messung des Dampf-Luft-Gehaltes in Trockenkammern," Melliand, 33, 10/1952 at p. 967.

Primary Examiner—Larry I. Schwartz
Assistant Examiner—David W. Westphal
Attorney, Agent, or Firm—Finnegan, Henderson, Farabow, Garrett & Dunner

[57] ABSTRACT

A device for determining the concentration of condensable vapor in a flowing gas stream which includes a gas evacuation conduit for receiving a sample of gas from the stream, a gas condenser in the evacuation conduit for condensing out essentially all of the condensable vapors in the sample and a gas flowmeter connected to the gas discharge of the gas condenser for determining the flow of the dry gas sample exiting the condenser. A pump is provided for withdrawing a sample of gas from the flowing gas stream and for conveying this sample at a constant, known volumetric flow through conduit and to the gas condenser and the flowmeter and a control means operatively connected to the flowmeter determines the condensable vapor concentration by comparing the flow of the dry gas sample with the known volumetric flow fed to the condenser.

12 Claims, 3 Drawing Figures

APPARATUS FOR DETERMINING THE CONCENTRATION OF VAPORS IN A FLOWING GAS STREAM

FIELD OF THE INVENTION

The invention relates to apparatus for determining the concentration of vapors in a flowing gas stream. More particularly, this invention relates to a device for continuously determining and controlling the concentration of water vapor in the drying air of a tobacco airflow drier.

BACKGROUND OF THE INVENTION

Accurate determination of the concentration of water vapor in the exhaust-air of a drier, for instance a tobacco airflow drier, is essential for several reasons. The water vapor concentration in many cases will strongly effect the chemical and physical properties of the material being dried and therefore it must be accurately regulated by appropriately regulating the volume of exhaust or intake air and/or the supply of additional vapor. Furthermore, the economy of an air drying process is primarily determined by the ratio of hot air to vapor and, for a constant mass flow, the terminal humidity of the material being dried can be regulated by a heater if the water vapor concentration of the exhaust air is known.

German Offenlegungsschrift No. 3 114 712 shows a tobacco airflow drier where the value of the concentration of water vapor in the exhaust air is ascertained by an Assmann aspiration-psychometer, termed therein as a "wet-ball measuring instrument". This instrument, however, does not allow a highly accurate determination of the condensing gases or vapors and moreover it is quite sensitive to soiling by dust or condensates formed in this instrument. Also the response time of this type of measuring instrument is relatively long.

A further type of instrument for measuring vapor-content is shown in German Auglegeschrift No. 2 846 826, in which a part of the substance being tested is placed in a measuring tube. Then the temperature, pressure and gas volume of the contents of the measuring tube, after settling for a time, is determined. This is a discontinuous process, however, unsuited to the necessity of continuously regulating a drying process.

Lastly an apparatus of this type for determining the concentrations of condensing as well as non-condensing gases or vapors in a process-gas flow is known from an article entitled "Direct Measurement of the Vapor-Air Content in Drying Chambers" [DIREKTE MESSUNG DES DAMPF-LUFT-GEHALTES IN TROCKENKAMMERN], published in Melliand, 33, 10/1952 at page 967. This includes a gas-evacuation conduit connected to the process gas flow, a gas condenser in the gas evacuation conduit, a continuously operating gas volumeter connected to the gas discharge of the gas condenser, a device to withdraw a sample of test gas from the process gas flow and to move this sample of test gas through the gas condenser and the gas volumeter, and a device to ascertain the concentrations in the measured amount of gas. The sample of test gas is cooled in the gas condenser to about 20° C. and the condensate above the dew point contained therein is removed and quantitatively measured in a graduated measuring glass. The residual air saturated with water vapor passes through a gas flowmeter acting as a gas volumeter. Therefore, on the basis of the temperature measured before and after the gas flowmeter, it is possible to determine the amount of gas and condensate.

This vapor-content test instrument suffers from the drawback that it is relatively expensive because the temperature and the pressure must also be determined in addition to the amounts of gas and condensates. The related computations are laborious and the measurement is discontinuous. Accordingly this instrument is unsuited to regulate the parameters of a continuous drying process.

SUMMARY OF THE INVENTION

Therefore it is the object of the invention to provide a new and improved apparatus for continuously determining the concentrations of condensable gases or vapors in a flowing gas stream that overcomes the limitations of the prior art devices.

Another object of this invention is to provide an apparatus that operates in a simple, continuous, and accurate manner so that there is practically a delayless determination of the vapor content of the flow of process gas, whereby the operational parameters of an industrial processing facility, for instance a tobacco airflow drier, can be accurately and continuously regulated.

These objects can be achieved by providing a device for determining the concentration of condensable vapor in a flowing gas stream which includes a gas evacuation conduit for receiving a sample of gas from the stream, a gas condenser in the evacuation conduit for condensing out essentially all of the condensable vapors in the sample and a gas flowmeter connected to the gas discharge of the gas condenser for determining the flow of the dry gas sample exiting the condenser. Means are provided for withdrawing a sample of gas from the flowing gas stream and for conveying this sample at a constant, known volumetric flow through conduit and to the gas condenser and the flowmeter. A control means operatively connected to the flowmeter determines the condensable vapor concentration by comparing the flow of the dry gas sample through the flowmeter with the known volumetric flow fed to the condenser and can generate suitable output signals relative to the vapor concentration to control the parameters of an industrial gas processing facility.

DETAILED DESCRIPTION OF THE INVENTION

It is to be understood that both the foregoing general description and the following detailed description are exemplary and explanatory but are not restrictive of the invention. The present invention will now be described in detail by reference to the accompanying drawings.

Figure 1:
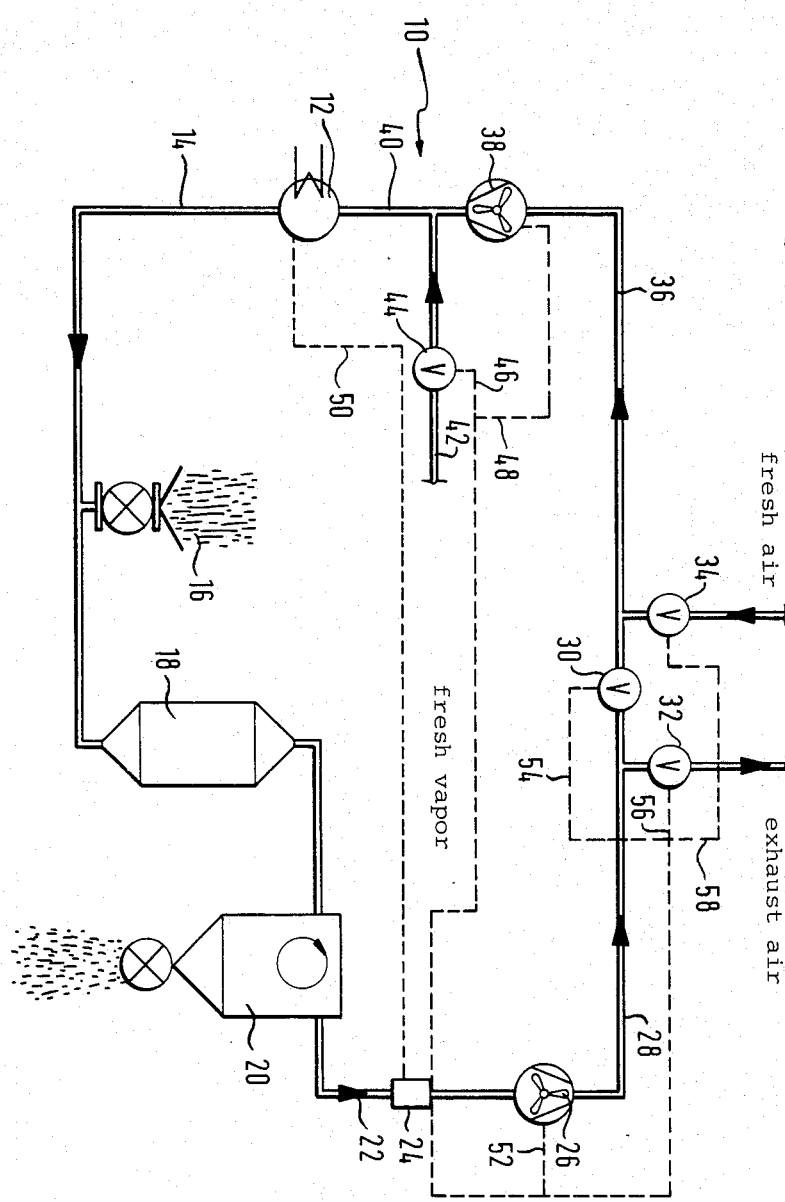
FIG. 1 shows schematically a typical tobacco airflow drier using the vapor content measuring device of the present invention for regulating its operational parameters.

A tobacco airflow drier is schematically shown in FIG. 1 and, generally denoted by 10, typically includes a heater 12 for heating the flow of drying gas, essentially air and water vapor, and a discharge conduit 14 from heater 12. The heated air in conduit 14 is supplied with tobacco from a suitable device 16 and the tobacco is thereafter dried in a drying region 18. Following drying, the tobacco is discharged from drier 18 by a cyclone 20, the flow of air leaving cyclone 20 through a discharge conduit 22 and into a device 24 for measuring the vapor content of the airflow. Next the flow of air is moved by a blower 26 through a conduit 28, a valve 30, a conduit 36 and a further blower 38 back to heater 12.

A discharge line for exhausting air is connected to conduit 28 between valve 30 and blower 26, the removal of which is controlled by a valve 32. A fresh air line is also provided for feeding fresh air into conduit 36 between valve 30 and blower 38, the supply of which is controlled by valve 34. Lastly a fresh vapor feed line 42 is connected through a valve 44 to conduit 40 between blower 38 and the entry to heater 12.

Depending on the value of the measurement of the vapor content in the drying air and the output signal generated thereby by device 24, the speeds of blowers 26 and 38, the flow rates of valves 30, 32, 34 and 44 as well as the temperature of heater 12 are all set so that the particular desired operating conditions are continuously maintained. The control paths between the measuring device 24 and the elements 44, 38, 12, 26, 30, 32 and 34 to be controlled by it are schematically indicated by the dashed lines 46, 48, 50, 52, 54, 56 and 58, respectively.

In view of the design of the tobacco airflow drier 10, the values for the speeds of the blowers 26 and 38, the settings of the valves 30, 32, 34 and 44 and the temperature of the heater 12 are determined and are so adjusted according to the actual value of the vapor content of the air passing through the vapor content measuring device 24 so that optimum drying of the tobacco with the hot mixture of air and water vapor is achieved in every case.

Figure 2:
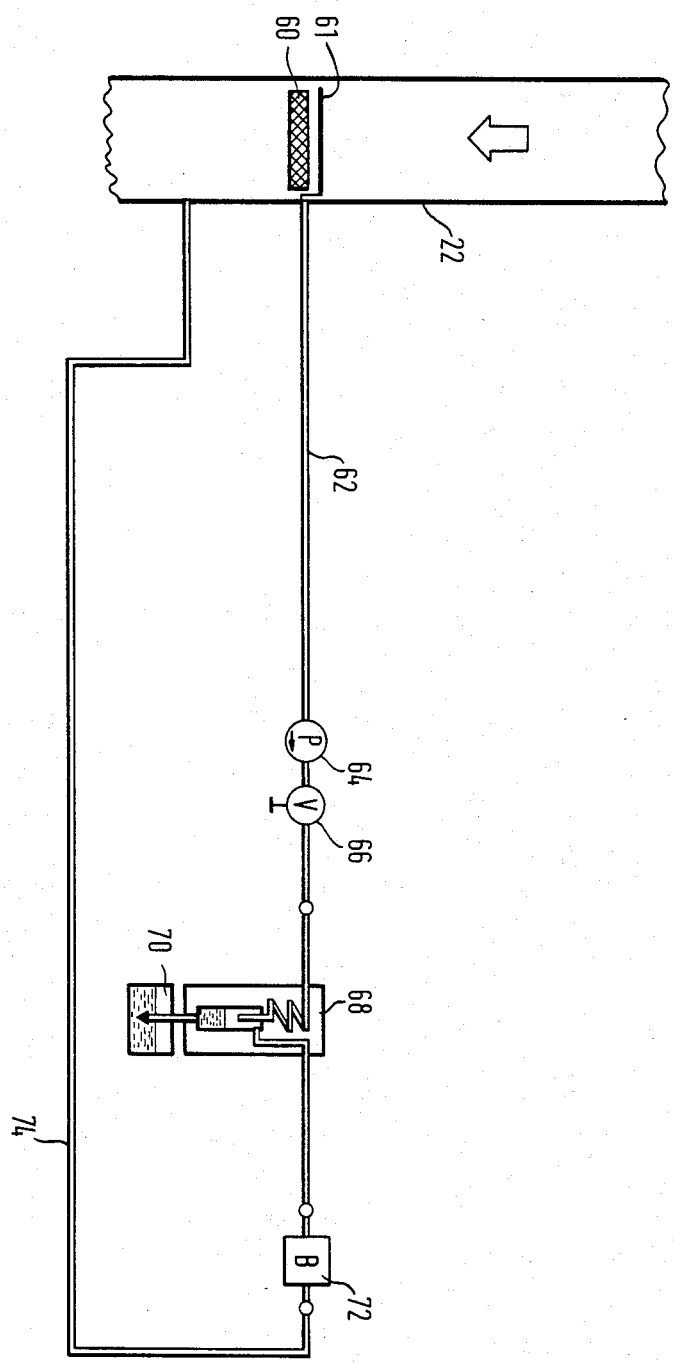
FIG. 2 is a schematic view of one embodiment of the vapor content measuring device.

FIG. 2 shows a first embodiment of the vapor content measuring device 24 of this invention. It includes a coarse filter 60 in the flow of process gas for purifying the flow of gas and is mounted in the discharge conduit 22 of cyclone 20 together with a dust-deflecting baffle 61 ahead of the coarse filter 60 as seen in FIG. 2.

A sample gas evacuation conduit 62 is connected to conduit 22 near filter 60 and dust-deflecting baffle 61. In accordance with the invention means are provided for withdrawing a sample of air or gas from discharge conduit 22 and for conveying this sample through the conduit to a gas condenser. As embodied this means comprises a pump 64 in conduit 62 and a control valve 66, which together force an approximately constant volumetric flow of sample gas into a gas condenser 68 kept at a temperature of about 5° C. so that the condenser will condense out all of the components of the flow of process gas that will condense at +5° C. Preferably gas-condenser 68 is an electric compressor. The condensate is then collected in a collecting vessel 70.

A flowmeter 72 is connected to the discharge side of dry gas condenser 68 and continuously measures the amount of gas leaving the gas condenser 68. After it leaves the flowmeter 72, the flow of gas is returned through a return line 74 into conduit 22. Volumetric flowmeter 72 can be either a thermal flowmeter or a measuring turbine. Control means 75 are connected to flowmeter 72 that determines the concentration of condensable vapors in the drying air by comparing the flow of dry gas through flowmeter 72 with the known volumetric flow fed to condenser 68 and generates an output signal relative to this determined concentration.

In the typical operation of the tobacco airflow drier 10 shown in FIG. 1, the flow of process gas, in this case air, would be at a temperature of between 100° and 200° C. and be reduced in pressure by about 20 mbars. The pump 64 pulls in a sample of the air flow through conduit 62 from the conduit 22. To prevent condensation of the condensable components in this sample before it reaches condenser 68, conduit 62 has thermostatically controlled means for keeping the conduit at the same temperature or at around 200° C. The pump 64 can be heated and thus should also be kept at a temperature up to 200° C., to prevent any condensation in the area of the pump. A membrane vacuum-pump with a capacity of up to about 10 liters/minute is suitable for use as pump 64.

The condensate discharge of gas condenser 68 is connected in such a manner with collecting vessel 70 for the condensate, that no gas can enter or escape for this would effect the results. For that purpose the collecting vessel 70 is placed underneath gas condenser 68, the condensate discharge of the gas condenser 68 being connected by a hose with collecting vessel 70. The height of the water column, that is the vertical height of the hose between the condensate discharge and the condensate level in the collecting vessel 70 is set to prevent escape from or entry into this area by the gas.

Accordingly the pump 64 with valve 66 conveys a precisely defined, constant flow of sample gas which still contains all the condensable vapors to gas condenser 68 which in turn is set to condense out all of the condensable ingredients. The amount of the residual, dry gas is then determined in volumetric flowmeter 72. The volume of flow passing through volumetric flowmeter 72 can then be used to determine the vapor content in the original sample by suitable control means that compares the measured volumetric flow rate with the known constant conveyed rate of pump 64. Since the volume of flow passing into condenser 68 is kept constant, the volume of flow of dry gas passing through meter 72 will be directly proportional to the vapor content of the gas and thus can be used directly to generate the required output signal of the control means. This output signal is then used to regulate the essential operational parameters of the tobacco airflow drier 10, as already explained in relation to FIG. 1.

The embodment of FIG. 2 is especially suited for the case where the pressure of the flow of process gas or air is subject only to slight fluctuations in conduit 22 so that pump 64 can force a constant, known volumetric flow into gas condenser 68. If the tobacco airflow drier 10 is so designed that the pressure of the flow of process gas is high enough with little pressure variation through conduit 22, then, it might even be possible to eliminate pump 64, because the pressure of the flow of process gas will be sufficient with valve 66 to force a constant, known volumetric flow into gas condenser 68. The pump 64 should be used, however, where the pressure of the flow gas is at or below atmospheric pressure.

Figure 3:
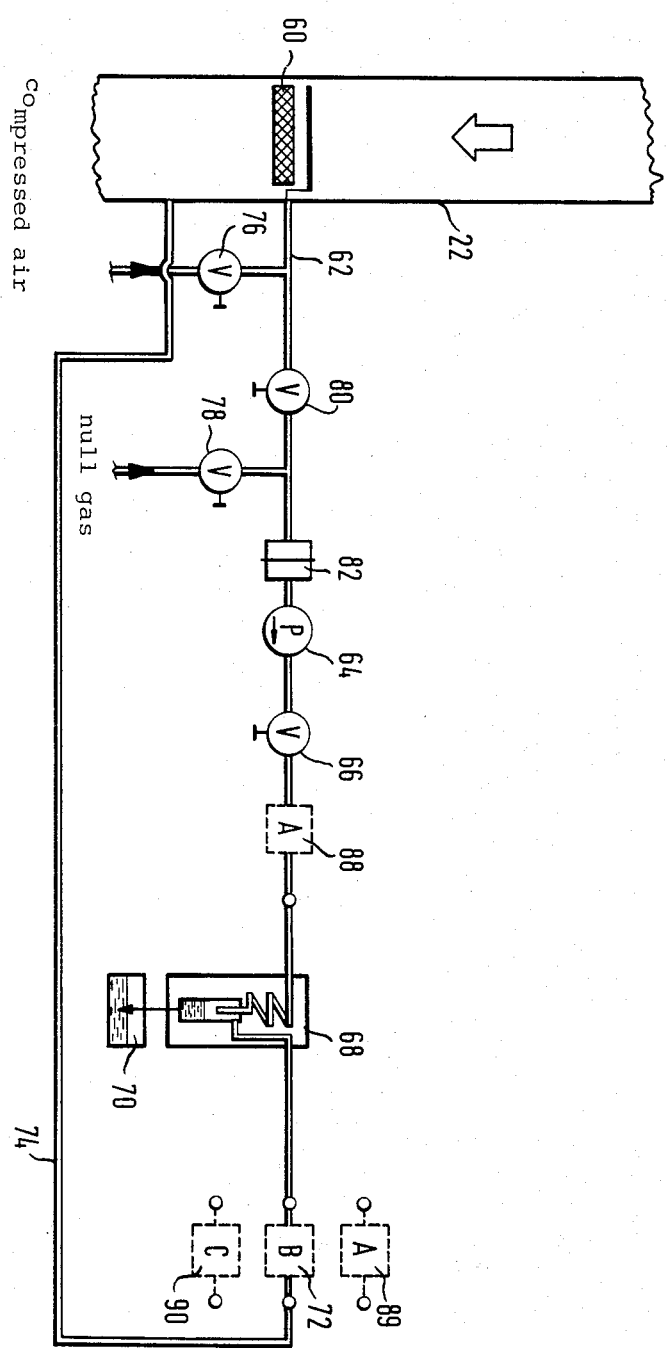
FIG. 3 is a schematic view of another embodiment of the device of this invention.

FIG. 3 shows another embodiment of the vapor content measuring device that can be used where there is significant pressure fluctuations in the flow of process gas and/or there are high dust loads. In this case means for cleansing coarse filter 60 are also provided.

Like numbers are used in FIG. 3 to indicate parts of the device that are common to the device of FIG. 2. In addition a compressed air line is connected through a valve 76 to the beginning of the sample gas evacuation conduit 62 and a valve 80 and a heated fine-filter 82 are provided in conduit 62. Another valve 78 connects a supply line for a dry gas flow between valve 80 and fine filter 82 to enable an operator to set the null point of the device. A mass flowmeter 88 and valve 66 to set the null point are provided between pump 64 and the intake to gas condenser 68.

To avert clogging of coarse filter 60 after relatively long operation and high dust loads, this coarse filter may be blown clean by closing valve 80 and opening valve 76 to periodically pass compressed air into conduit 62 and 22.

Valve 80 also is closed when the null point of the vapor content device is being set and when dry null gas is being supplied through valve 78. A predetermined flow rate is set by means of the adjustable valve 66 and corresponds in turn to a given display of flowmeter 72 connected to the discharge of gas condenser 68.

Nulling can be automated by rinsing at given time intervals with the null gas. A regulator, not shown in further detail, can be used together with the valve 66 to set the corresponding reference value of the flow rate. This automatic null adjustment is appropriate where there is danger that the obstruction to flow created by filter 60 or filter 82 can substantially vary the flow rates due to high dust loads over appreciable lengths of time.

Mass flowmeter 88 determines the mass of the flow of process gas fed by the pump 64 to the gas condenser 68. The volumetric flowmeter 72 already used in the embodiment of FIG. 2 can be used or be replaced as needed by a mass flowmeter 89 or by a flow rate meter 90. In any case and similar to the embodiment of FIG. 2, the difference between the amount of gas fed to gas condenser 68, in this case as determined by mass flowmeter 88, and the amount of the dry sample gas after removal of the condensable components by gas condenser 68, as determined by mass flowmeter 89, volumetric flowmeter 72 or flow rate meter 90, represents the amount of condensable vapors, i.e. water vapor in the drying air of the tobacco airflow drier 10. When the ascertained mass, the volumetric flow or the rate of the volumetric flow is subtracted from the input mass flow and the difference divided by the input mass flow, this represents the percentage of condensable vapors, in this ase water vapor, in the process gas.

Where necessary the condensate collected in collecting vessel 70 may be analyzed to detect impurities or other significant substances in the tobacco in the drying air.

In this embodiment also the entire gas sampling part from conduit 22 to at least as far as pump 64 and preferably as far as mass flowmeter 88 should be thermostatically controlled to prevent any premature condensation of vapors in this region and to assure that the ascertained difference represents an accurate measurement of the vapor content of the flow of process gas.

The advantages achieved by the invention rest on the following operation: In either embodiment, a constant volumetric flow moves into the gas condenser which condenses all vapors condensing at +5° C. so that the gas volumeter 72 connected to the gas discharge of the gas condenser 68 measures only the flow rate of the dry sample of test gas sample. Using the known constant volumetric flow of the mixture of gas and vapor, the proportion of the condensable and noncondensable gases or vapors can be readily computed.

Accordingly, the output signal of the control means is a direct representation of the content of vapor and can be used directly to regulate the essential control members of the processing facility.

The device responds extremely rapidly to minor changes in the vapor content, whereby corresponding adjustments in the processing can take place practically without delay resulting in an optimum regulation of the overall facility.

By using appropriate filters as shown, interference by particles can be practically excluded and because the condensable vapors are removed prior to measuring, interference from condensate components is also virtually excluded. Therefore very little maintenance is required even after long periods of operation.

Furthermore, it is possible to automate cleaning of the coarse filter and to set the null-point by supplying the compressed air or the gas to set the null-point at given time intervals.

The invention in its broader aspects is not limited to the specific details shown and described and departures may be made from such details without departing from the scope of the invention or sacrificing its chief advantages.

What is claimed is:

1. A device for determining the concentration of condensable vapor in a flowing gas stream comprising
   (a) a gas evacuation conduit for receiving a sample of gas from the stream;
   (b) a gas condenser in the evacuation conduit for condensing out essentially all of the condensable vapors in the sample;
   (c) a gas flowmeter connected to the gas discharge of the gas condenser for determining the flow of the dry gas sample exiting the condenser;
   (d) means for withdrawing a sample of gas from the flowing gas stream and for conveying this sample at a constant, known volumetric flow through the gas evacuation conduit and to the gas condenser and the flowmeter; and
   (e) control means operatively connected to the flowmeter that determines the condensable vapor concentration by comparing the flow of the dry gas sample through the flowmeter with the known volumetric flow fed to the condenser.

2. The device of claim 1, in which an electric compressor gas condenser is used as the gas condenser and which condenses all vapors that condense above 5° C.

3. The device of claim 1, wherein the means for withdrawing the sample of gas from the stream and conveying it to the condenser includes a pump connected to the evacuation conduit.

4. The device of claim 3, wherein the pump is a thermostatically controlled membrane vacuum-pump.

5. The device of claim 3, including a mass flowmeter mounted between the pump and the gas condenser for measuring the flow of gas sample fed to the condenser.

6. The device of claim 1, including a heated filter in the gas evacuation conduit.

7. The device of claim 1, wherein the condensate discharge of the gas condenser is sealed in a gas-tight manner.

8. The device of claim 1, wherein the gas flowmeter is a mass flowmeter, a volumetric flowmeter or a rate flowmeter.

9. The device of claim 1, including means for thermostatically controlling the gas temperature of the gas evacuation conduit to prevent premature condensation of the condensable vapors.

10. The device of claim 1, including means for periodically injecting compressed air into the gas evacuation conduit to cleanse the conduit.

11. The device of claim 1, including means for supplying a dry gas to the conduit to adjust the null point of the device.

12. In a tobacco airflow drier for air drying tobacco having air blowers, valves and heaters for producing, controlling, and heating a drying air stream, the improvement comprising a device for determining the concentration of condensable water vapor in the drying air stream comprising a gas evacuation conduit for receiving a sample of gas from the drying air, a gas condenser in the evacuation conduit for condensing out essentially all of the condensable vapors in the sample, a gas flowmeter connected to the gas discharge of the gas condenser for determining the flow of the dry gas sample exiting the condenser, means for withdrawing a sample of gas from the drying air and for conveying this sample at a constant, known volumetric flow through the gas evacuation conduit and to the gas condenser and the flowmeter and control means operatively connected to the flowmeter that determines the condensable vapor concentration by comparing the flow of the dry gas sample through the flowmeter with the known volumetric flow fed to the condenser, said control means generating an output signal relative to the determined concentration of water vapor for selectively controlling the speed of the blowers, the opening of the valves and the temperature of the heaters to continuously regulate the water vapor content of the drying air stream.

* * * * *